US008812108B2

(12) United States Patent
Shuros et al.

(10) Patent No.: US 8,812,108 B2
(45) Date of Patent: Aug. 19, 2014

(54) AUTONOMIC BALANCE MONITORING TO CONTROL INTERMITTENT THERAPY

(75) Inventors: Allan C. Shuros, St. Paul, MN (US); Shantha Arcot-Krishnamurthy, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1246 days.

(21) Appl. No.: 12/396,132

(22) Filed: Mar. 2, 2009

(65) Prior Publication Data

US 2009/0234409 A1 Sep. 17, 2009

Related U.S. Application Data

(60) Provisional application No. 61/036,421, filed on Mar. 13, 2008.

(51) Int. Cl.
*A61N 1/08* (2006.01)
*A61N 1/365* (2006.01)

(52) U.S. Cl.
USPC .............................................. 607/17; 607/11

(58) Field of Classification Search
USPC ...................................................... 607/11, 17
See application file for complete search history.

(56) References Cited

U.S. PATENT DOCUMENTS

| 2002/0165586 | A1 | 11/2002 | Hill et al. |
|---|---|---|---|
| 2003/0191403 | A1 | 10/2003 | Zhou et al. |
| 2004/0186525 | A1 | 9/2004 | Burnes et al. |
| 2005/0065443 | A1 | 3/2005 | Ternes |
| 2006/0253156 | A1 | 11/2006 | Pastore et al. |
| 2007/0150005 | A1 | 6/2007 | Sih et al. |
| 2007/0213773 | A1 | 9/2007 | Hill et al. |
| 2007/0239210 | A1 | 10/2007 | Libbus et al. |
| 2007/0255345 | A1 | 11/2007 | Krause |
| 2007/0260283 | A1 | 11/2007 | Li |
| 2007/0260285 | A1 | 11/2007 | Libbus et al. |
| 2008/0183231 | A1* | 7/2008 | Sathaye et al. .................... 607/9 |

OTHER PUBLICATIONS

"International Application Serial No. PCT/US2009/001321, International Search Report mailed Jul. 2, 2009", 4 pgs.
"International Application Serial No. PCT/US2009/001321, Written Opinion mailed Jul. 2, 2009", 7 pgs.
Schmidt, G., et al., "Heart-rate turbulence after ventricular premature beats as a predictor of mortality after acute myocardial infarction", *The Lancet*, 353, (1999), 1390-1396.
Schwab, J. O., et al., "Influence of basic heart rate and sex on heart rate turbulence in healthy subjects.", *Pacing Clin Electrophysiol.*, 27(12), (2004), 1625-1631.

* cited by examiner

*Primary Examiner* — Tammie K Heller
(74) *Attorney, Agent, or Firm* — Schwegman Lundberg & Woessner, P.A.

(57) ABSTRACT

Various system embodiments comprise a myocardial stimulator, at least one sensor adapted for use in detecting heart rate to determine heart rate turbulence (HRT), and a controller connected to the myocardial stimulator and the at least one sensor. The myocardial stimulator is adapted to deliver pacing pulses through at least one electrode to provide cardiac pacing. The controller is adapted to intermittently deliver a sequence of stress-inducing pacing pulses adapted to increase sympathetic tone during the stress-inducing pacing. The controller is further adapted to determine HRT from the detected heart rate to assess cardiac stress to the stress-inducing pacing pulses, and adjust at least one parameter of the stress-inducing pacing pulses to adjust cardiac stress if the cardiac stress to the stress-inducing pacing pulses is undesirable.

24 Claims, 9 Drawing Sheets

AUTONOMIC BALANCE MONITORING TO CONTROL INTERMITTENT THERAPY

CROSS-REFERENCE TO RELATED APPLICATION

This application claims the benefit of U.S. Provisional Application No. 61/036,421, filed on Mar. 13, 2008, under 35 U.S.C. §119(e), which is hereby incorporated by reference.

TECHNICAL FIELD

This application relates generally to medical devices and, more particularly, to systems, devices and methods for monitoring autonomic balance to control intermittent therapy.

BACKGROUND

Heart disease such as myocardial infarction and/or heart failure can cause adverse ventricular remodeling and an imbalance in autonomic tone favoring sympathetic activity over parasympathetic tone. During heart disease, the compromised ventricles may be less than capable of maintaining normal cardiac output. As a result, the body compensates for the reduced cardiac output by increasing sympathetic tone and suppressing parasympathetic activity, resulting in increased heart rate, myocardial contractility and blood volume. This mechanism is acutely beneficial, but has a long-term deleterious effect.

It has been shown experimentally that intermittent stress such as exercise, dobutamine infusion, myocardial pacing, or external counterpulsation provides beneficial conditioning effects for the heart and body. Intermittent stress (e.g. exercise) improved the imbalance in the autonomic tone, as the autonomic tone trended from a predominantly sympathetic tendency toward a desired autonomic balance between the sympathetic and parasympathetic systems. For example, intensive exercise training in patients with reduced ventricular function has been shown to result in a significant improvement in exercise capacity (increased $O_2$ uptake, maximum minute ventilation, $CO_2$ production, exercise time and watts), with no deleterious effects on left ventricular volume, function or wall thickness. A potential mechanism for the benefit may be that these short intervals of stress increase sympathetic tone and cause a reflexive increase in parasympathetic tone after the stress is discontinued.

Intermittent sympathomimetic stimulation in animals with dobutamine produces benefits analogous to those of physical conditioning. In a pilot clinical study, patients with stable moderate severe HF (EF=23%) who received dobutamine therapy (30 min/day, 4 days/week, 3 weeks) experienced the following benefits: increased exercise tolerance; improved heart rate variability; lowered peripheral vascular resistance; and reduced plasma noradrenaline.

It has been proposed to deliver intermittent stress in the form of artificial cardiac pacing as a potential therapy for cardiac disease. A patient may not experience the desired benefit if the pacing delivers too little stress, or may be harmed (similar to over-exercising) if the pacing delivers too much stress.

SUMMARY

Various system embodiments comprise a myocardial stimulator, at least one sensor adapted for use in detecting heart rate to determine heart rate turbulence (HRT), and a controller connected to the myocardial stimulator and the at least one sensor. The myocardial stimulator is adapted to deliver pacing pulses through at least one electrode to provide cardiac pacing. The controller is adapted to intermittently deliver a sequence of stress-inducing pacing pulses adapted to increase sympathetic tone during the stress-inducing pacing. The controller is further adapted to determine HRT from the detected heart rate to assess cardiac stress to the stress-inducing pacing pulses, and adjust at least one parameter of the stress-inducing pacing pulses to adjust cardiac stress if the cardiac stress to the stress-inducing pacing pulses is undesirable.

Various system embodiments comprise means for intermittently delivering a sequence of stress-inducing pacing pulses adapted to increase sympathetic tone during the stress-inducing pacing, means for assessing cardiac stress to the stress-inducing pacing pulses, wherein the means for assessing cardiac stress includes means for assessing HRT and means for adjusting at least one parameter of the stress-inducing pacing pulses to adjust cardiac stress if the cardiac stress to the stress-inducing pacing pulses is undesirable.

According to various method embodiments, a sequence of stress-inducing pacing pulses is intermittently delivered. The stress-inducing pacing pulses are adapted to increase sympathetic tone during the stress-inducing pacing. Cardiac stress due to the stress-inducing pacing pulses is assessed. Assessing cardiac stress includes determining HRT. If the assessed cardiac stress to the stress-inducing pacing pulses is undesirable, at least one parameter of the stress-inducing pacing pulses is adjusted to adjust cardiac stress.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
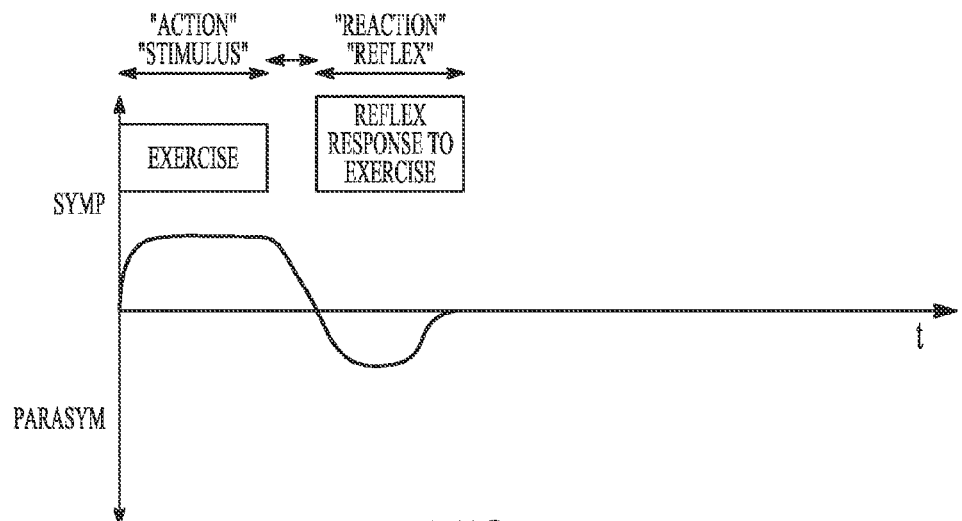
FIG. 1 illustrates the autonomic response to a period of exercise.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter effectively measures a patient's physiological response to the cardiac protective pacing therapy (CPPT) to control therapy delivery. CPPT is intermittently delivered to intermittently provide a desired stress to the heart, as evidenced by an increase in sympathetic tone during the pacing. CPPT may also be referred to as an intermittent pacing therapy (IPT) to condition the heart.

Various implantable device embodiments provide closed-loop control for an intermittent pacing therapy for conditioning effect, where a patient's response to intermittent therapy is measured to determine whether the patient is able to tolerate the current stress or is able to tolerate more stress. If it is determined that the patient is able to tolerate more stress, and the pacing therapy determines it is desirable to increase the stress for the intermittent pacing therapy, the present subject matter performs pacing according to a protocol to increase the asynchrony of the heart, where the increased asynchrony (less coordination) provides more stress to the heart. If it is determined that the patient is unable to tolerate the current stress or that the current stress is otherwise undesirable, the present subject mater performs the pacing according to a protocol to decrease the asynchrony of the heart for the intermittent pacing therapy, where the decreased asynchrony (more coordination) lowers the stress to the heart.

HRT has been found to be a very effective surrogate measure of autonomic tone. A preceding heart rate influences HRT. A lower preceding heart rate produces a higher HRT. During strenuous exercise in normal patients where there is increased sympathetic tone, there is a corresponding decrease in HRT. Schmidt et al. found the absence of HRT after ventricular premature beats is a very potent postinfarction risk stratifier that is independent of other known risk factors and which is stronger than other presently available risk predictors. For example, an increased HRT, for a short-term assessment of a response to CPPT, indicates a fairly healthy status. That is, although it is desired to continue CPPT therapies to trend the autonomic balance toward a more parasympathetic tone, the increased HRT for the short-term assessment indicates that the patient's health is such that the patient is able to tolerate the current CPPT protocol.

Some device embodiments deliver closed-loop intermittent pacing therapy by assessing HRT before, during and after intermittent stress therapy to assess the efficacy of the stimulation and to make automatic adjustments to stimulation parameters to increase, decrease or maintain the stress therapy (e.g. duration and/or intensity of the stress). The present subject matter can determine whether to maintain the therapy settings if desired, or to increase the stress level of the CPPT closer to the patient's threshold for tolerating the therapy or lower the stress level of the CPPT to allow the patient to better tolerate the therapy. For example, a more aggressive therapy (increase stress) may be delivered by shortening the AV delay, pacing at a faster rate, providing longer periods of pacing, or providing longer VV delays (e.g. a longer time between a right ventricular pace and a left ventricular pace as there is normally very little time delay between the two). A more conservative therapy (decrease stress) may be delivered by lengthening the AV delay, pacing at a slower rate, providing shorter periods of pacing, or providing shorter VV delays.

Various embodiments use HRT, as a short-term autonomic balance estimate, to provide closed-loop feedback control of CPPT. Various device embodiments introduce an extra systolic pace, also referred to as a premature ventricular contraction (PVC), in response to a triggering event. Examples of triggering events include the expiration of a timer at programmed intervals, or based on an electrogram event such as a detected tachyarrhythmia. The HRT response, indicative of autonomic balance and cardiac health, to the PVC is measured. The cardiac pacing is modulated based on the measured HRT. A decreased HRT indicates a worsening health status; and various embodiments of the present subject matter discontinue pacing or deliver more conservative pacing in response to determining that the measured HRT reflects a decreased HRT. An increased HRT indicates improving health status; and various embodiments of the present subject matter deliver a more aggressive pacing in response to determining that the measured HRT reflects an increased HRT. Various embodiments continue the current settings of the pacing if there is no change in the HRT. Some implantable device embodiments record a baseline HRT response template by providing an artificially paced PVC while the patient is at rest. Following a pacing session, such as a steady-state session, the device inserts a paced PVC, measures the resulting HRT, and compares the measured HRT to the HRT response template.

Various embodiments use HRT to assess both shorter-term and longer-term effects of the therapy. For example, it is expected that the long-term trend of the CPPT is to improve the autonomic balance by increasing the parasympathetic tone and decreasing the sympathetic tone. The efficacy of therapy to provide the desired trend of improving autonomic balance is monitored by measuring HRT during periods of non-pacing. The short-term assessment monitors the cardiac ability to take the induced stress as part of the long term therapy. The short-term assessment is measured between short bouts of intermittent stress delivery, or is otherwise measured in a time frame with respect to the CPPT that assesses the cardiac stress response to the sequence of stress-inducing pacing pulses. During a time of CPPT, there are periods of time during which cardiac pacing is delivered, and periods of time during which cardiac pacing is not delivered. For example, CPPT may be delivered for 10-60 minutes for 1 to 3 times a day. A short term assessment of HRT can be made during the periods of time during which cardiac pacing is not delivered to stress the heart. For example, HRT may be assessed during each period between successive pacing times, or may be assessed after every 2nd, 3rd, etc. pacing period. For example, 10 minutes of CPPT may be delivered to begin the CPPT session. The CPPT is stopped for a time to measure HRT, and make an assessment of how well the patient is able to tolerate the CPPT, before continuing with the CPPT session.

CPPT may be referred to as a cardiac or myocardial conditioning therapy as it modulates autonomic tone to improve autonomic balance for the heart. Cardiac conditioning therapy may be used in a heart failure therapy, a hypertension therapy, or a post-MI therapy (treatment for remodeling).

Physiology

Provided below is a brief discussion of the nervous system and some diseases capable of being treated using the present subject matter. This discussion is believed to assist a reader in understanding the disclosed subject matter.

Nervous System

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

The heart rate and force is increased when the sympathetic nervous system is stimulated, and is decreased when the sympathetic nervous system is inhibited (the parasympathetic nervous system is stimulated). Cardiac rate, contractility, and excitability are known to be modulated by centrally mediated reflex pathways. Baroreceptors and chemoreceptors in the heart, great vessels, and lungs, transmit cardiac activity through vagal and sympathetic afferent fibers to the central nervous system. Activation of sympathetic afferents triggers reflex sympathetic activation, parasympathetic inhibition, vasoconstriction, and tachycardia. In contrast, parasympathetic activation results in bradycardia, vasodilation, and inhibition of vasopressin release. Among many other factors, decreased parasympathetic or vagal tone or increased sympathetic tone is associated with various arrhythmias genesis, including ventricular tachycardia and atrial fibrillation.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Clusters of nerve cells can be referred to as autonomic ganglia. These nerve cells can also be electrically stimulated to induce a baroreflex, which inhibits the sympathetic nerve activity and stimulates parasympathetic nerve activity. Autonomic ganglia thus forms part of a baroreflex pathway. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of vessel wall (e.g. arterial wall).

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

Neural stimulation can be used to stimulate nerve traffic or inhibit nerve traffic. An example of neural stimulation to stimulate nerve traffic is a lower frequency signal (e.g. within a range on the order of 20 Hz to 50 Hz). An example of neural stimulation to inhibit nerve traffic is a higher frequency signal (e.g. within a range on the order of 120 Hz to 150 Hz). Other methods for stimulating and inhibiting nerve traffic have been proposed. According to various embodiments of the present subject matter, sympathetic neural targets include, but are not limited to, a peroneal nerve, a sympathetic column in a spinal cord, and cardiac post-ganglionic sympathetic neurons. According to various embodiments of the present subject matter, parasympathetic neural targets include, but are not limited to, a vagus nerve, a baroreceptor, and a cardiac fat pad. Neural stimulation can be selectively delivered to afferent neural pathways, selectively delivered to efferent neural pathways, or delivered to both afferent and efferent neural pathways. For example, some embodiments selectively stimulate or inhibit only parasympathetic afferents or only parasympathetic efferents, and some embodiments selectively stimulate or inhibit sympathetic afferents or efferents.

CPPT

As identified above, autonomic tone may be modulated by stimulating or inhibiting an autonomic neural target. Embodiments of the present subject mater modulate autonomic tone using CPPT. Physiology associated with CPPT is discussed below.

The sinoatrial (SA) node generates electrical impulses that propagate through an electrical conduction system to various regions of the heart to excite the myocardial tissues of these regions. An intrinsic heart rhythm may be a normal rhythm or an abnormal rhythm. Coordinated delays in the propagations of the electrical impulses in a normal electrical conduction system causes the various portions of the heart to contract in synchrony. Synchrony, as used herein, indicates a coordinated contraction of the various portions of the heart to result in efficient pumping functions. Synchrony does not indicate that all of the portions of the heart contract at the same time.

Abnormal electrical conduction and/or deteriorated myocardial tissue cause asynchrony (no coordinated timing) between the various portions of the heart, which result in inefficient pumping functions. The present subject matter relates to systems, devices and methods for modulating autonomic tone. The present subject matter uses cardiac protective pacing therapy (CPPT) and neural stimulation to provide a cardiac conditioning therapy to improve autonomic balance, and thus improve the health of the heart. CPPT is an intermittent pacing therapy that paces the heart in such a manner as to intentionally stress the heart during intermittent periods. When the heart is stressed with CPPT, the heart is paced to force the heart to work harder in comparison to a time when CPPT is not applied to the heart. The paced heart works harder in local regions of the heart away from a site where the stress-inducing pacing pulses are delivered. For example, a stressed heart may be paced to beat faster and/or more asynchronous (less coordinated). By way of example and not limitation, various CPPT embodiments increase the pacing rate for the right atrium, increase the pacing rate for the right ventricle, shorten an AV delay, and/or lengthen the VV delay. Increasing the intensity of the CPPT may involve further increasing the pacing rate of the right atrium or right ventricle, further shortening the AV delay to be more different from the intrinsic rate without CPPT, altering the pacing site, and/or further lengthening of the VV delay to be more different from the intrinsic rate without CPPT. In patients who have dysynchrony and receive biventricular pacing for the dysynchrony, cardiac stress can be increased by discontinuing the biventricular pacing during the sequence of stress inducing pacing pulses. Decreasing the intensity of the CPPT may involve altering the pacing site, may involve reducing the pacing rate of the right atrium or right ventricle closer to the intrinsic rate, may involve increasing the AV delay closer to the intrinsic AV delay, and/or may involve shortening the VV delay closer to the intrinsic VV delay (whether or not the intrinsic rhythm is normal or abnormal). Delivering CPPT with higher intensity (not stress) corresponds to increasing the sympathetic response during the CPPT.

Diseases

The present subject matter can be used to prophylactically or therapeutically treat various diseases by modulating autonomic tone. Examples of such diseases or conditions include hypertension, cardiac remodeling, and heart failure.

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction (decompensation). It has been shown that the extent of ventricular remodeling is positively correlated with increased mortality in post-MI and heart failure patients.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease. Heart failure patients have reduced autonomic balance, which is associated with LV dysfunction and increased mortality. Modulation of the sympathetic and parasympathetic nervous systems has potential clinical benefit in preventing remodeling and death in heart failure and post-MI patients. Direct electrical stimulation can activate the baroreflex, inducing a reduction of sympathetic nerve activity and reducing blood pressure by decreasing vascular resistance. Sympathetic inhibition and parasympathetic activation have been associated with reduced arrhythmia vulnerability following a myocardial infarction, presumably by increasing collateral perfusion of the acutely ischemic myocardium and decreasing myocardial damage.

HRT

The present subject matter uses HRT as an autonomic balance indicator (ABI). HRT is the physiological response of the sinus node to a premature ventricular contraction (PVC), consisting of a short initial heart rate acceleration followed by a heart rate deceleration. HRT has been shown to be an index of autonomic function, closely correlated to HRV. HRT is believed to be an autonomic baroreflex. The PVC causes a brief disturbance of the arterial blood pressure (low amplitude of the premature beat, high amplitude of the ensuing normal beat). This fleeting change is registered immediately with an instantaneous response in the form of HRT if the autonomic system is healthy, but is either weakened or missing if the autonomic system is impaired.

By way of example and not limitation, it has been proposed to quantify HRT using Turbulence Onset (TO) and Turbulence Slope (TS). TO refers to the difference between the heart rate immediately before and after a PVC, and can be expressed as a percentage. For example, if two beats are evaluated before and after the PVC, TO can be expressed as:

$$TO\% = \frac{(RR_{+1} + RR_{+2}) - (RR_{-2} + RR_{-1})}{(RR_{-2} + RR_{-1})} * 100.$$

$RR_{-2}$ and $RR_{-1}$ are the first two normal intervals preceding the PVC and $RR_{+1}$ and $RR_{+2}$ are the first two normal intervals following the PVC. In various embodiments, TO is determined for each individual PVC, and then the average value of all individual measurements is determined. However, TO does not have to be averaged over many measurements, but can be based on one PVC event. Positive TO values indicate deceleration of the sinus rhythm, and negative values indicate acceleration of the sinus rhythm. The number of R-R intervals analyzed before and after the PVC can be adjusted according to a desired application. TS, for example, can be calculated as the steepest slope of linear regression for each sequence of five R-R intervals. In various embodiments, the TS calculations are based on the averaged tachogram and expressed in milliseconds per RR interval. However, TS can be determined without averaging. The number of R-R intervals in a sequence used to determine a linear regression in the TS calculation also can be adjusted according to a desired application.

Rules or criteria can be provided for use to select PVCs and for use in selecting valid RR intervals before and after the PVCs. A PVC event can be defined by an R-R interval in some interval range that is shorter than a previous interval by some time or percentage, or it can be defined by an R-R interval without an intervening P-wave (atrial event) if the atrial events are measured. Various embodiments select PVCs only if the contraction occurs at a certain range from the preceding contraction and if the contraction occurs within a certain range from a subsequent contraction. For example, various embodiments limit the HRT calculations to PVCs with a minimum prematurity of 20% and a post-extrasystole interval which is at least 20% longer than the normal interval. Additionally, pre-PVC R-R and post-PVC R-R intervals are considered to be valid if they satisfy the condition that none the of the beats are PVCs. One HRT process, for example, excludes RR intervals that are less than a first time duration, that are longer than a second time duration, that differ from a preceding interval by more than a third time duration, or that differ from a reference interval by a predetermined amount time duration or percentage. In an embodiment of such an HRT process with specific values, RR intervals are excluded if they are less than 300 ms, are more than 2000 ms, differ from a preceding interval by more than 200 ms, or differ by more than 20% from the mean of the last five sinus intervals. Various embodiments of the present subject matter provide programmable parameters, such as any of the parameters identified above, for use in selecting PVCs and for use in selecting valid RR intervals before and after the PVCs.

When an ABI is desired to assess the ability of the patient to tolerate the stress from the CPPT, the device introduces a PVC, and measures the resulting HRT, as described above.

Benefits of using HRT to monitor autonomic balance include the ability to measure autonomic balance at a single moment in time. Additionally, unlike the measurement of HRV, HRT assessment can be performed in patients with frequent atrial pacing. Further, HRT analysis provides for a simple, non-processor-intensive measurement of autonomic balance. Thus, data processing, data storage, and data flow are relatively small, resulting in a device with less cost and less power consumption. Also, HRT assessment is faster than HRV, requiring much less R-R data. HRT allows assessment over short recording periods similar in duration to typical neural stimulation burst durations, such as on the order of tens of seconds, for example.

Other ABIs

An ABI can be used to provide closed-loop control of the therapy to adjust autonomic tone. Various embodiments assess ABI using one or various combinations of parameters, such as heart rate variability (HRV), heart rate turbulence (HRT), electrogram features, activity, respiration, and pulmonary artery pressure. These parameters are briefly discussed below. Various embodiments provide closed loop control of the treatment using ABI.

HRV is one technique that has been proposed to assess autonomic balance. HRV relates to the regulation of the sinoatrial node, the natural pacemaker of the heart by the sympathetic and parasympathetic branches of the autonomic nervous system. An HRV assessment is based on the assumption that the beat-to-beat fluctuations in the rhythm of the heart provide us with an indirect measure of heart health, as defined by the degree of balance in sympathetic and vagus nerve activity.

The time interval between intrinsic ventricular heart contractions changes in response to the body's metabolic need for a change in heart rate and the amount of blood pumped through the circulatory system. For example, during a period of exercise or other activity, a person=s intrinsic heart rate will generally increase over a time period of several or many heartbeats. However, even on a beat-to-beat basis, that is, from one heart beat to the next, and without exercise, the time interval between intrinsic heart contractions varies in a normal person. These beat-to-beat variations in intrinsic heart rate are the result of proper regulation by the autonomic nervous system of blood pressure and cardiac output; the absence of such variations indicates a possible deficiency in the regulation being provided by the autonomic nervous system. One method for analyzing HRV involves detecting intrinsic ventricular contractions, and recording the time intervals between these contractions, referred to as the R-R intervals, after filtering out any ectopic contractions (ventricular contractions that are not the result of a normal sinus rhythm). This signal of R-R intervals is typically transformed into the frequency-domain, such as by using fast Fourier transform (FFT) techniques, so that its spectral frequency components can be analyzed and divided into low and high frequency bands. For example, the low frequency (LF) band can correspond to a frequency (f) range $0.04 \text{ Hz} < f < 0.15 \text{ Hz}$, and the high frequency (HF) band can correspond to a frequency range $0.15 \text{ Hz} < f < 0.40 \text{ Hz}$. The HF band of the R-R interval signal is influenced only by the parasympathetic/ vagal component of the autonomic nervous system. The LF band of the R-R interval signal is influenced by both the sympathetic and parasympathetic components of the autonomic nervous system. Consequently, the ratio LF/HF is regarded as a good indication of the autonomic balance between sympathetic and parasympathetic/vagal components of the autonomic nervous system. An increase in the LF/HF ratio indicates an increased predominance of the sympathetic component, and a decrease in the LF/HF ratio indicates an increased predominance of the parasympathetic component. For a particular heart rate, the LF/HF ratio is regarded as an indication of patient wellness, with a lower LF/HF ratio indicating a more positive state of cardiovascular health. A spectral analysis of the frequency components of the R-R interval signal can be performed using a FFT (or other parametric transformation, such as autoregression) technique from the time domain into the frequency domain. Such calculations require significant amounts of data storage and processing capabilities. Additionally, such transformation calculations increase power consumption, and shorten the time during which the implanted battery-powered device can be used before its replacement is required.

One example of an HRV parameter is SDANN (standard deviation of averaged NN intervals), which represents the standard deviation of the means of all the successive 5 minutes segments contained in a whole recording. Other HRV parameters can be used.

Various embodiments extract various ECG features to provide an ABI. Examples of such features include heart rate, which can be used to form HRV, and heart rate turbulence. Other features can be extracted from the ECG, and one or various combinations of these features can be used to provide an ABI. Various embodiments provide blood pressure to provide an ABI. For example, some embodiments sense pulmonary artery blood pressure.

Activity sensors can be used to assess the activity of the patient. Sympathetic activity naturally increases in an active patient, and decreases in an inactive patient. Thus, activity sensors can provide a contextual measurement for use in determining the autonomic balance of the patient. Various embodiments, for example, provide a combination of sensors to trend heart rate and/or respiration rate to provide an indicator of activity.

Two methods for detecting respiration involve measuring a transthoracic impedance and minute ventilation. Respiration can be an indicator of activity, and can provide an explanation of increased sympathetic tone. For example, it may not be appropriate to change or modify a treatment for modulating autonomic tone due to a detected increase in sympathetic activity attributable to exercise.

Respiration measurements (e.g. transthoracic impedance) can also be used to measure Respiratory Sinus Arrhythmia (RSA). RSA is the natural cycle of arrhythmia that occurs through the influence of breathing on the flow of sympathetic and vagus impulses to the sinoatrial node. The rhythm of the heart is primarily under the control of the vagus nerve, which inhibits heart rate and the force of contraction. The vagus nerve activity is impeded and heart rate begins to increase when a breath is inhaled. When exhaled, vagus nerve activity increases and the heart rate begins to decrease. The degree of fluctuation in heart rate is also controlled significantly by regular impulses from the baroreceptors (pressure sensors) in the aorta and carotid arteries. Thus, a measurement of autonomic balance can be provided by correlating heart rate to the respiration cycle.

Therapy Protocols

The present subject matter modulates autonomic tone using CPPT. Preconditioning of the myocardium occurs as a prophylactic therapy in preparation for an anticipated event. For example, the myocardium can be preconditioned in anticipation for surgery, or can be preconditioned based on observed or detected events that indicate an increased probability of an upcoming ischemic event. Examples of such events include a previous myocardial infarction and angina. Prophylactic conditioning can be used to modulate autonomic tone from higher sympathetic tendencies toward an autonomic balance to improve the health of a patient prone to heart failure, hypertension and remodeling. Postconditioning of the myocardium occurs as a therapeutic treatment to a disease. For example, postconditioning of the myocardium can reduce the size of any infarct area caused by the ischemic event. For example, the postconditioning therapy can be triggered based on commands received from a patient or physician after observing a myocardial infarction, or a physician can deliver postconditioning therapy after a surgical procedure for which the heart was stopped. In an embodiment, the device detects an ischemic event or other event indicated for postconditioning therapy, and automatically delivers the postconditioning therapy. The postconditioning therapy can occur during the time of reperfusion, for a time after reperfusion, or during and for a time after reperfusion.

A cardiac conditioning therapy may also be referred to as a cardiac protective therapy, as it is protects against the deleterious effects of an autonomic tone with an undesirably high sympathetic tendency. The cardiac conditioning therapy may mimic the effects of exercise.

FIG. 1 illustrates the autonomic response to a period of exercise. Exercise is a stimulus that increases the sympathetic response. After the period of exercise ends, a reflex response to the exercise increases the parasympathetic tone. The parasympathetic response appears to be a reaction to the sympathetic action of exercise. Those of ordinary skill in the art will understand that the illustrated graph is a simple illustration. The horizontal axis represents time, and the vertical axis represents the autonomic tone. For simplicity, the value of the vertical axis corresponding to the horizontal axis represents the autonomic balance (the balance between the sympathetic and parasympathetic neural activity). Those of ordinary skill in the art will know that, over time, as the health of the heart improves and the autonomic balance improves by having a more parasympathetic tone, the horizontal axis (representing the autonomic balance) will trend more toward the parasympathetic tone. By way of an everyday example of exercise, it is noted that a runner's resting heart rate tends to lower as the runner's conditioning improves. This example indicates that running, which temporarily increases sympathetic tone as evidenced by an increased heart rate, will trend the autonomic balance of the runner toward a more parasympathetic tone.

Figure 2:
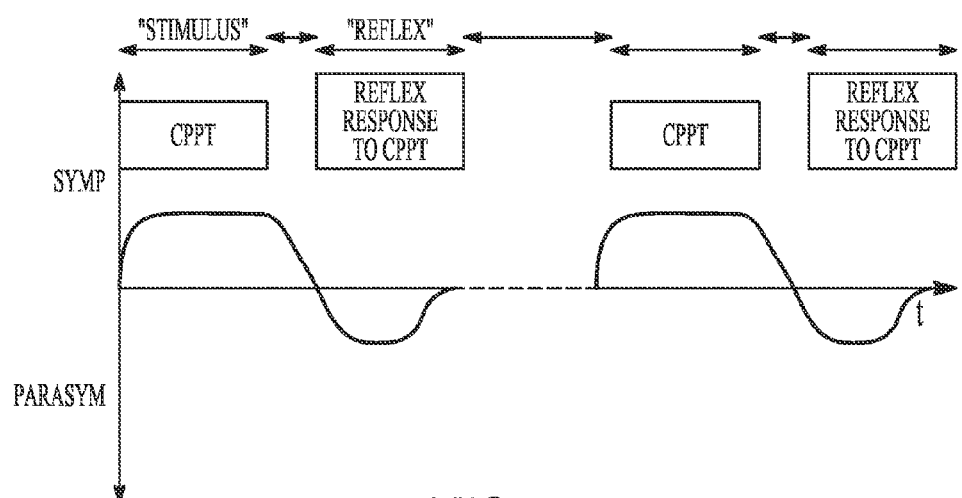
FIG. 2 illustrates the autonomic response to a period of cardiac protective pacing therapy (CPPT).

FIG. 2 illustrates the autonomic response to a period of CPPT. Similar to the period of exercise, CPPT is a stimulus that increases the sympathetic response during the period of pacing, and results in a reflex response that increases parasympathetic tone after the pacing ends. As illustrated, the CPPT functions as a stimulus that provides a sympathetic component (action) that generates a desired parasympathetic reflex (reaction to the action). A cardiac conditioning therapy may correspond to recommended exercises periods (e.g. 30 to 60 minutes, two times per day). Various therapy durations and frequencies can be used. Various cardiac conditioning therapies are programmed according to a schedule. Various cardiac conditioning therapies are programmed to occur after a detected event such as a period of exercise by the patient.

Figure 3:
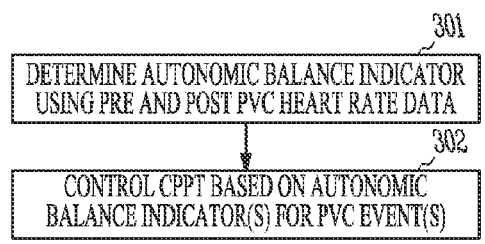
FIG. 3 illustrates an embodiment to control CPPT.

FIG. 3 illustrates an embodiment to control CPPT. At 301, an ABI (HRT) is determined using pre and post-PVC heart rate data. At 302, CPPT is controlled based on at least one PVC event.

Figure 4:
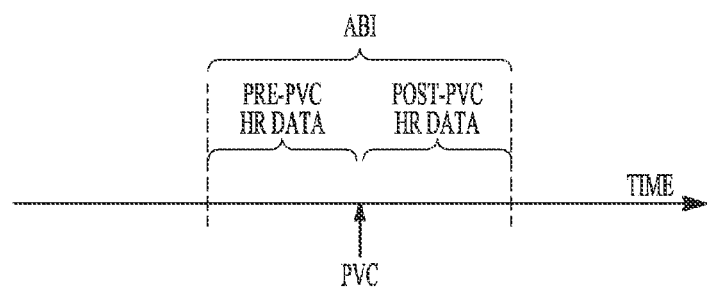
FIG. 4 illustrates a timeline with a premature ventricular contraction (PVC) event, pre-PVC heart rate data, and post-PVC heart rate data.

FIG. 4 illustrates a timeline with a PVC event, pre-PVC heart rate data, and post-PVC heart rate data. HRT is delivered using pre-PVC and post-PVC data. As illustrated in the figure, an ABI value is determined by pre-PVC heart rate data and post-PVC heart rate data. According to various embodiments, the illustrated pre-PVC heart rate data includes a predetermined number of R-R intervals (e.g. 2 beats) that immediately precede the PVC event; and the illustrated post-PVC heart rate data includes a predetermined number of R-R intervals (e.g. 2 beats) that immediately follow the PVC event. HRT can be measured periodically or intermittently and recorded.

Figure 5:
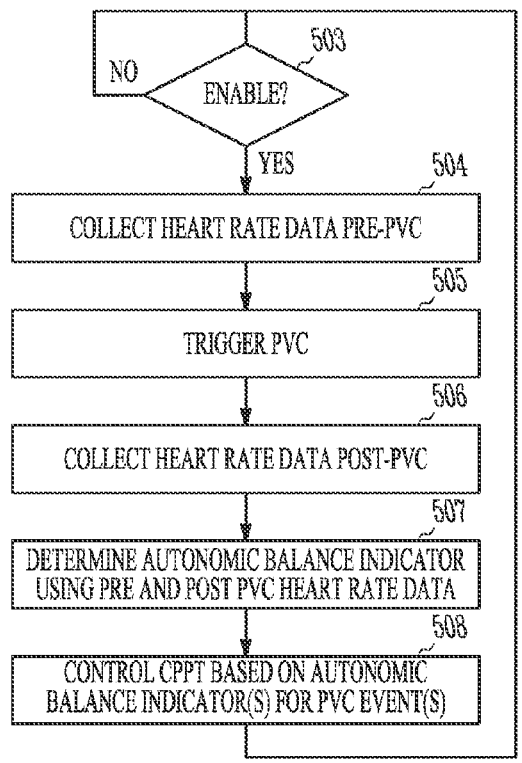
FIG. 5 illustrates a method for determining an autonomic balance indicator (ABI) for use in controlling CPPT, according to various embodiments of the present subject matter.

FIG. 5 illustrates a method for determining an ABI for use in controlling CPPT, according to various embodiments of the present subject matter. At 503, it is determined whether an enable signal has been received. The enable signal triggers the determination of HRT. The enable signal may be based on an event (e.g. the end of a sequence of stress-inducing pacing for CPPT) or based on a timer. In response to an enable signal, pre-PVC heart rate data is collected at 504. After initial pre-PVC heart rate data is collected, the process triggers a PVC at 505. HRT may be determined based on a detected intrinsic PVC. Various embodiments of the present subject matter provide a pace to cause the PVC at a desired time with respect to the CPPT to be able to assess the stress caused by the CPPT. Various embodiments only detect intrinsic PVCs, various embodiments only induce or stimulate PVCs, and various embodiments perform a process to detect intrinsic PVCs, and stimulate PVCs. After a PVC occurs, post-PVC heart rate data is collected at 506. At 507, the process determines an autonomic balance indicator (ABI) using the pre-PVC heart rate data and the post-PVC heart rate data. At 508, the CPPT is controlled to control the stress delivered to the heart based on the calculated ABI(s) for the PVC event(s). For example, the duration of the CPPT, the AV intervals, the VV intervals and/or the rate may be modified based on the calculated ABI(s).

Figure 6:
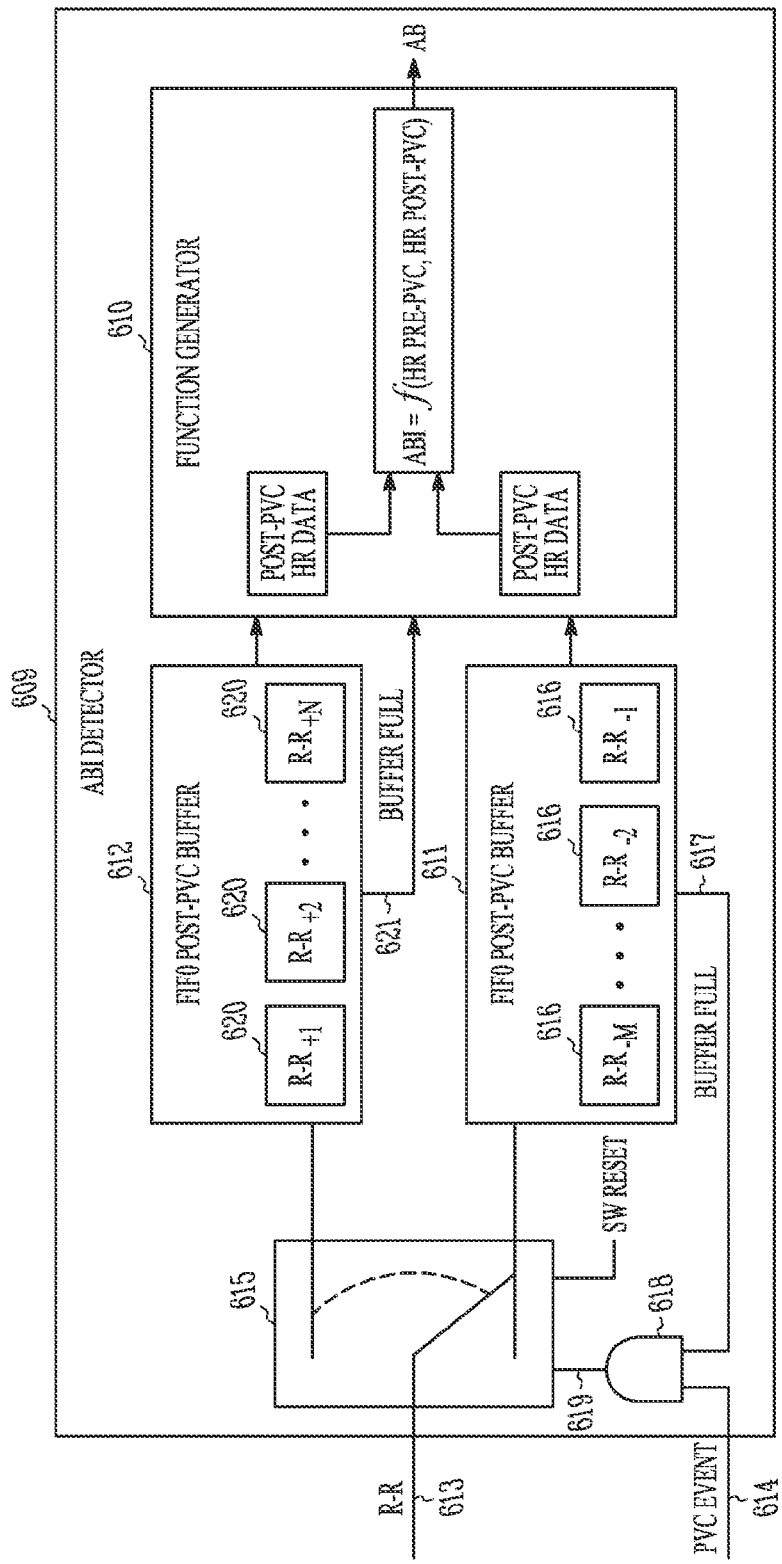
FIG. 6 illustrates an embodiment of an ABI detector.

FIG. 6 illustrates an embodiment of an ABI detector. The illustrated ABI detector 609 includes a function generator 610, a first-in, first-out (FIFO) pre-PVC buffer 611, a FIFO post-PVC buffer 612, an R-R detector input 613, and a PVC event detector input 614. When first enabled, successive R-R intervals are stored via switch 615 into the FIFO pre-PVC buffer 611. The buffer 611 can include different numbers of registers 616 to store the R-R intervals. For example, one embodiment includes two registers adapted to store two consecutive R-R intervals, and one embodiment includes five registers adapted to store five consecutive R-R intervals. Once the buffer 616 is full, the oldest R-R interval is removed from the buffer when the next R-R interval is received. Thus, the buffer stores a sequence of the latest R-R intervals such that, upon a PVC event, the buffer stores the intervals immediately preceding the PVC event. Additionally, an enable signal 617 is generated after the pre-PVC buffer is full, which indicates that the analyzer is ready to process a PVC event, and which also may be used to trigger a pace to cause the PVC. As illustrated by the AND logic gate 618, when the PVC event occurs and the enable signal is present, a signal is generated on line 619 to actuate the switch 615 and store subsequent R-R intervals in the FIFO post-PVC buffer 612. The buffer 612 can include different numbers of registers 620 to store the R-R intervals. For example, one embodiment includes two registers adapted to store two consecutive R-R intervals, and one embodiment includes five registers adapted to store five consecutive R-R intervals. When the buffer is full, the function generator 610 responds to an enable signal 621 to use the pre-PVC heart rate data stored in the pre-PVC buffer and the post-PVC heart rate data stored in the post-PVC buffer to generate an ABI value. The switch can be reset to begin to receive R-R intervals in the pre-PVC buffer in response to the next ABI enable signal.

Figure 7:
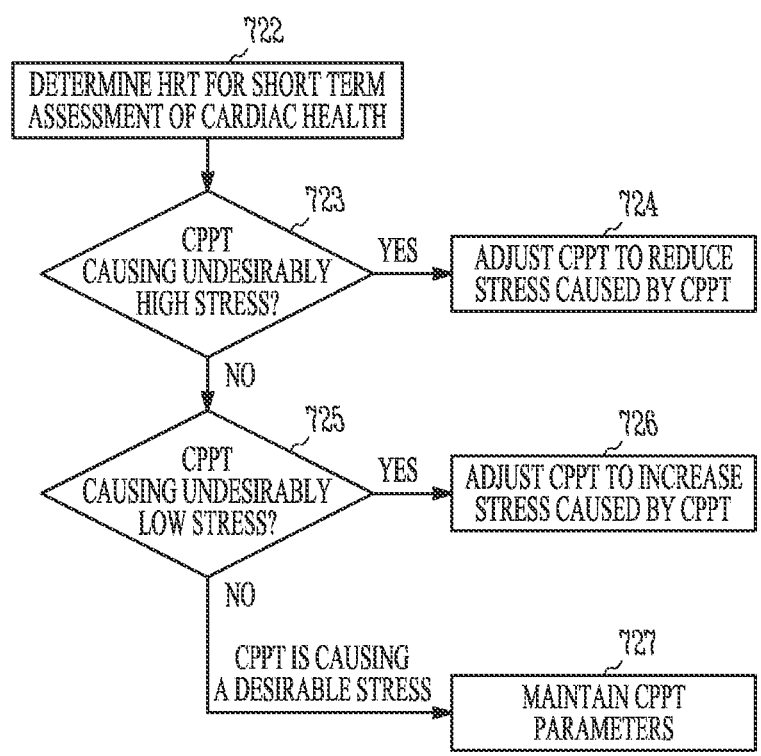
FIG. 7 illustrates an embodiment of a method for monitoring heart rate turbulence (HRT) to control CPPT.

FIG. 7 illustrates an embodiment of a method for monitoring HRT to control CPPT. At 722, an HRT is determined to provide a short-term assessment of cardiac health. The determination of HRT is appropriately timed to reflect the stress on the heart caused by the CPPT. At 723, it is determined using the HRT if the CPPT is causing an undesirably high stress to the heart. If it is determined that the CPPT is stressing the heart too much, parameter(s) of the CPPT is adjusted to reduce the cardiac stress caused by the CPPT, as illustrated at 724. At 725, it is determined using the HRT if the CPPT is causing an undesirably low stress to the heart. If it is determined that the CPPT is not stressing the heart enough, parameter(s) of the CPPT is adjusted to increase the cardiac stress caused by the CPPT, as illustrated at 726. If the CPPT is not causing an undesirably high stress at 723 and is not causing an undesirably low stress at 725, the current CPPT parameter(s) are maintained, as illustrated at 727. The illustrated order in the figure is provided as an example. Those of ordinary skill in the art will understand, upon reading and comprehending this disclosure, that logical modifications can be made and still appropriately assess the cardiac stress, and modulate the CPPT intensity to provide a desired stress.

The effect of the CPPT on autonomic balance can be viewed in the short term and the long term. The goal of a treatment is to trend the intrinsic autonomic balance to a desired tone (e.g. more parasympathetic tone). The intrinsic autonomic balance can be monitored during times which are not acutely affected by a sequence of stress-inducing pulses using a variety of techniques to assess ABI such has HRV, HRT, heart sounds, electrograms, and the like. These intrinsic autonomic balance indicators reflect the trend of the autonomic balance, (a long-term effect of the CPPT). The short-term assessment of autonomic balance is appropriately timed with respect to a sequence of stress-inducing pacing pulses to reflect the stress that the CPPT delivers during the sequence of pacing pulses.

Figure 8:
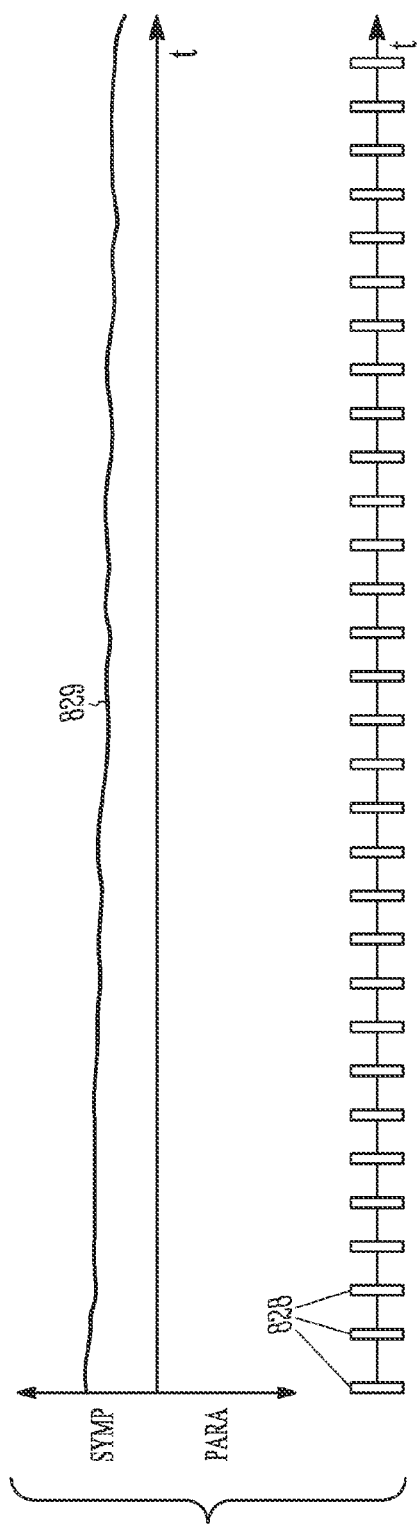
FIG. 8 illustrates a plurality of CPPT sessions and further illustrates an autonomic balance over the course of the CPPT sessions.

FIG. 8 illustrates a plurality of CPPT sessions and further illustrates an autonomic balance 829 over the course of the CPPT sessions. For example, each CPPT session may be delivered on the order of minutes to several hours. Each CPPT session temporarily increases the sympathetic tone. As illustrated, the goal of the CPPT treatment to increase the intrinsic parasympathetic tone/lower the intrinsic sympathetic tone over the course of multiple CPPT sessions. This is reflected by the trend (e.g. over the course of days, weeks, months) of the autonomic balance lower toward more parasympathetic tone.

Figure 9:
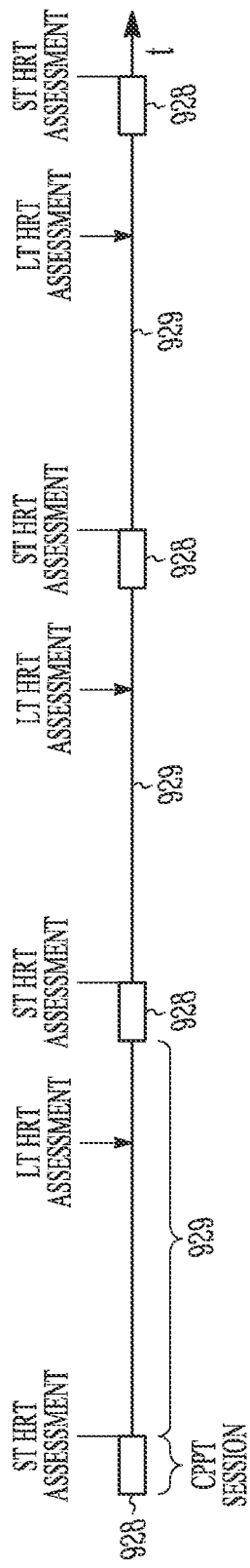
FIG. 9 illustrates, by way of example, timing for determining short term HRT assessments and long-term HRT assessments, according to various embodiments.

FIG. 9 illustrates, by way of example, timing for determining short term HRT assessments and long-term HRT assessments, according to various embodiments. The illustrated time line includes four CPPT sessions 928, during which a sequence of stress-inducing pacing pulses is delivered. The CPPT sessions 928 are separated by inter CPPT pacing periods 929, during which the sequence of stress-inducing pacing pulses is not delivered. In the illustrated time line, short-term HRT assessments are determined upon completion of the sequence of the sequence of stress-inducing pacing pulses, or soon thereafter, such as to reflect the stress caused by the stress-inducing pacing pulses. The short-term HRT assessments can be used to indicate the ability of the patient to endure the stress of the therapy. The long-term HRT assessments are illustrated as occurring toward the end of the inter CPPT pacing period, such as to reflect the intrinsic autonomic balance of the patient without an acute, significant reaction to the CPPT.

Figure 10:
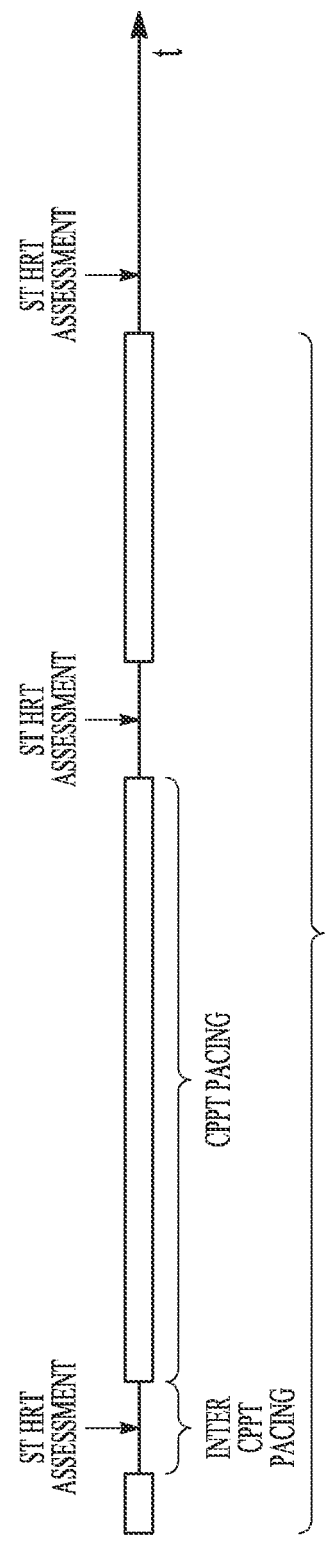
FIG. 10 illustrates an embodiment in which a CPPT session is interrupted to provide a short term HRT assessment before resuming the sequence of stress-inducing pacing pulses to complete the CPPT session.

FIG. 10 illustrates an embodiment in which a CPPT session 1028 is interrupted to provide a ST HRT assessment before resuming the sequence of stress-inducing pacing pulses to complete the CPPT session. For example, if a CPPT session is suppose to last for 60 minutes, the CPPT session may be interrupted after 10 minutes to assess the ability of the heart to continue with the CPPT session. A CPPT session may be interrupted multiple times.

Figure 11:
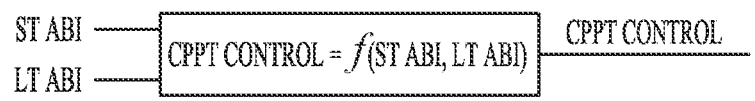
FIG. 11 illustrates a CPPT control generator, such as may be incorporated into a controller, according to various embodiments.

FIG. 11 illustrates a CPPT control generator, such as may be incorporated into a controller, according to various embodiments. The illustrated CPPT control generator receives at least one short-term ABI and at least one long-term ABI, and generates a CPPT control signal to modulate the intensity of the CPPT based on a function of at least one short-term ABI and at least one long-term ABI. Thus, the present subject matter can account for both the efficacy of the treatment toward the desired goal for the treatment, as well as the acute autonomic health of the patient in responding to the stress from the CPPT. The long-term ABI can be compared to a desired ABI goal for the treatment. For example, if the health of the patient allows more stress and more stress is desired to achieve an effective long-term treatment, embodiments of the present subject matter will increase the stress. As a further example, if more stress is desired to achieve an effective long-term treatment but the patient's health currently does not allow for the stress, embodiments of the present subject matter will not modify the CPPT to increase the stress. As yet another example, if more stress is desired to achieve an effective long-term treatment but the patient's current health only allows for a limited increase in stress rather than a desired full increase of stress for the long-term treatment, embodiments of the present subject matter limit the stress increase based on the patient's current health.

Figure 12:
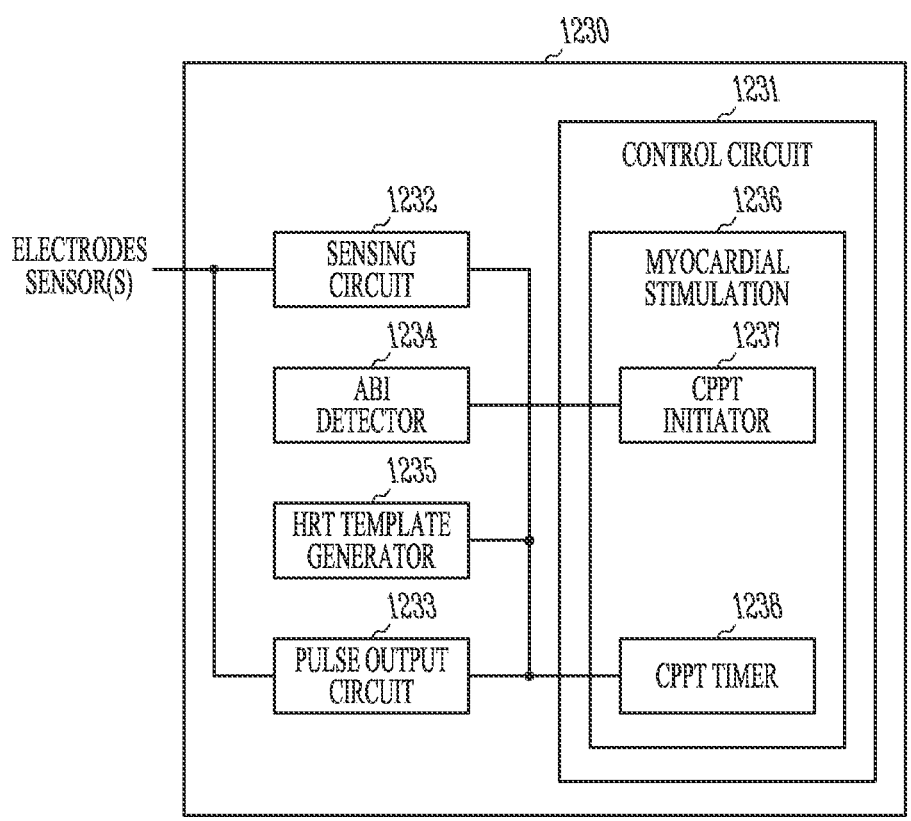
FIG. 12 illustrates an embodiment of an implantable medical device.

FIG. 12 illustrates an embodiment of an implantable medical device. The illustrated device 1230 includes a control circuit 1231, a sensing circuit 1232, a pulse output circuit 1233, an ABI detector 1234 and an HRT template generator 1235. The illustrated controller 1231 includes a myocardial stimulation module 1236, including a CPPT initiator 1237 used to control the beginning of a sequence of stress-inducing pulses and a CPPT timer 1238 used to control the duration of the sequence of stress-inducing pulses. The myocardial stimulation module 1236 is adapted to modify parameters of the CPPT, such as rate, AV interval, and/or VV interval. The stress inducing pulses are generated by the pulse output circuit 1233 to the electrodes. The sensing circuit 1232 is used to sense heart rate, which is used by the ABI detector to determine HRT. ABI detector and sensing circuit can cooperate to determine HRV or other ABIs as well. The HRT template generator creates and stores an HRT (such as an HRT during a time without CPPT) to provide a baseline to determine if the HRT is increasing or decreasing.

According to various embodiments, the control circuit allows the device to control the delivery of CPPT as well as other pacing therapies. This allows the function of CPPT pacing to be included in an implantable medical device that delivers pacing therapies on a long-term basis, such as for treatment of bradycardia and heart failure. In various embodiments, CPPT includes a temporary pacing therapy delivered for one or more brief periods according to a schedule and/or in response to an ABI, and the implantable medical device also delivers a chronic pacing therapy such as a bradycardia pacing therapy, or CRT. In other embodiments, the CPPT is the only pacing therapy delivered, or the CPPT is the only pacing therapy programmed to be delivered for at least a certain period of time.

Figure 13:
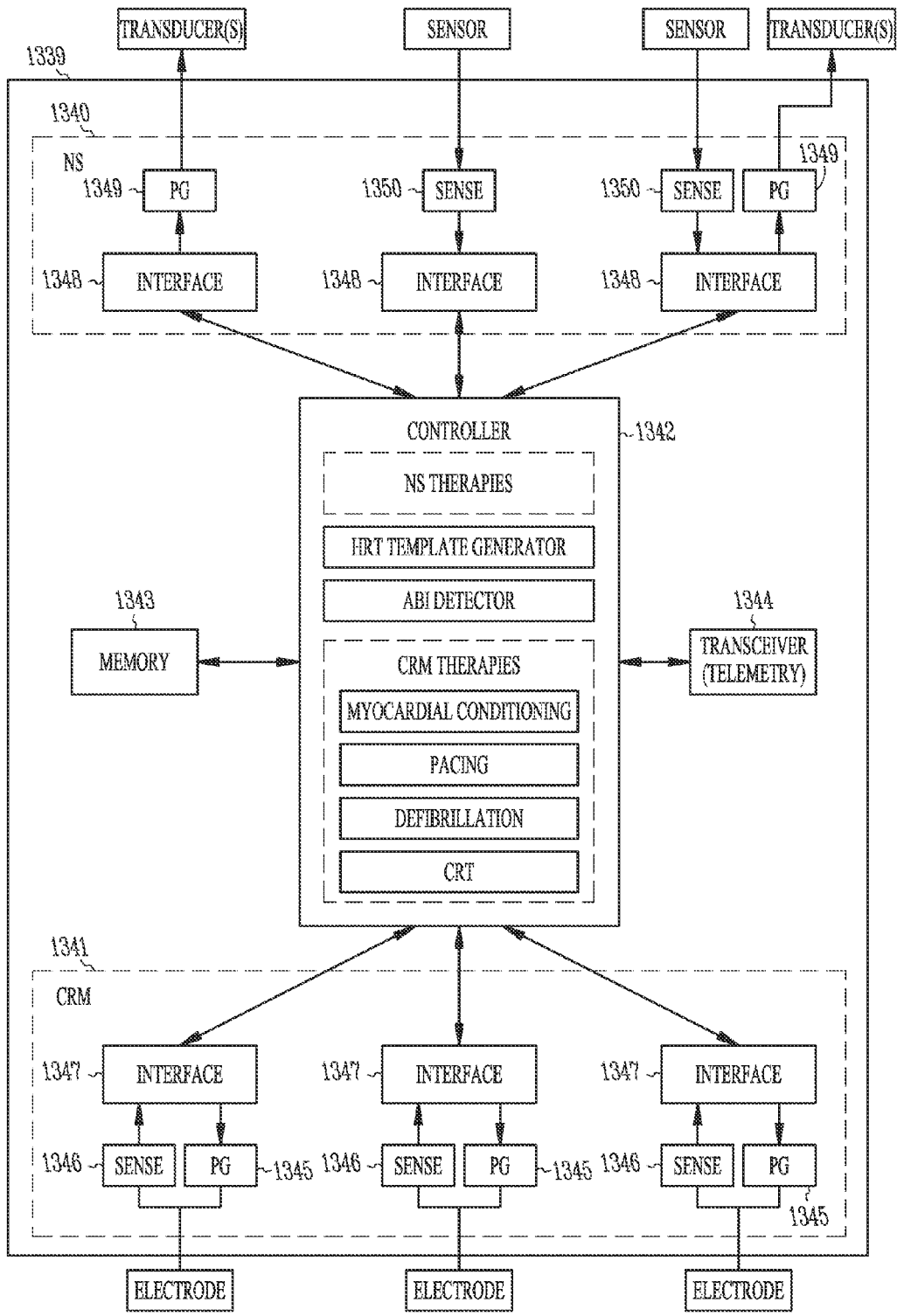
FIG. 13 illustrates an implantable medical device (IMD) having a neural stimulation (NS) component and cardiac rhythm management (CRM) component, according to various embodiments of the present subject matter.

FIG. 13 illustrates an implantable medical device (IMD) 1339 having a neural stimulation (NS) component 1340 and cardiac rhythm management (CRM) component 1341, according to various embodiments of the present subject matter. The illustrated device includes a controller 1342 and memory 1343. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. According to various embodiments, the controller includes a processor to execute instructions embedded in memory to perform the neural stimulation and CRM functions. CRM functions include myocardial conditioning (CPPT). Other examples of CRM functions include bradycardia pacing, antitachycardia therapies such as antitachycardia pacing and defibrillation, and CRT. The controller also executes instructions to detect ABI and, according to some embodiments, generate an HRT template. The illustrated device further includes a transceiver 1344 and associated circuitry for use to communicate with a programmer or another external or internal device. Various embodiments include a telemetry coil.

The CRM therapy section 1341 includes components, under the control of the controller, to stimulate a heart and/or sense cardiac signals using one or more electrodes. The CRM therapy section includes a pulse generator 1345 for use to provide an electrical signal through an electrode to stimulate a heart, and further includes sense circuitry 1346 to detect and process sensed cardiac signals. An interface 1347 is generally illustrated for use to communicate between the controller 1342 and the pulse generator 1345 and sense circuitry 1346. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 1340 includes components, under the control of the controller, to stimulate a neural stimulation target and in some embodiments sense parameters associated with nerve activity or surrogates of nerve activity such as blood pressure and respiration. Three interfaces 1348 are illustrated for use to provide neural stimulation. However, the present subject matter is not limited to a particular number of interfaces, or to any particular stimulating or sensing functions. Pulse generators 1349 are used to provide electrical pulses to transducer or transducers for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components or other signals. Sense circuits 1350 are used to detect and process signals from a sensor, such as a sensor of nerve activity, blood pressure, respiration, and the like. The interfaces 1348 are generally illustrated for use to communicate between the controller 1342 and the pulse generator 1349 and sense circuitry 1350. Each interface, for example, may be used to control a separate lead. Various embodiments of the NS therapy section only include a pulse generator to stimulate neural targets such as a vagus nerve.

Figure 14:
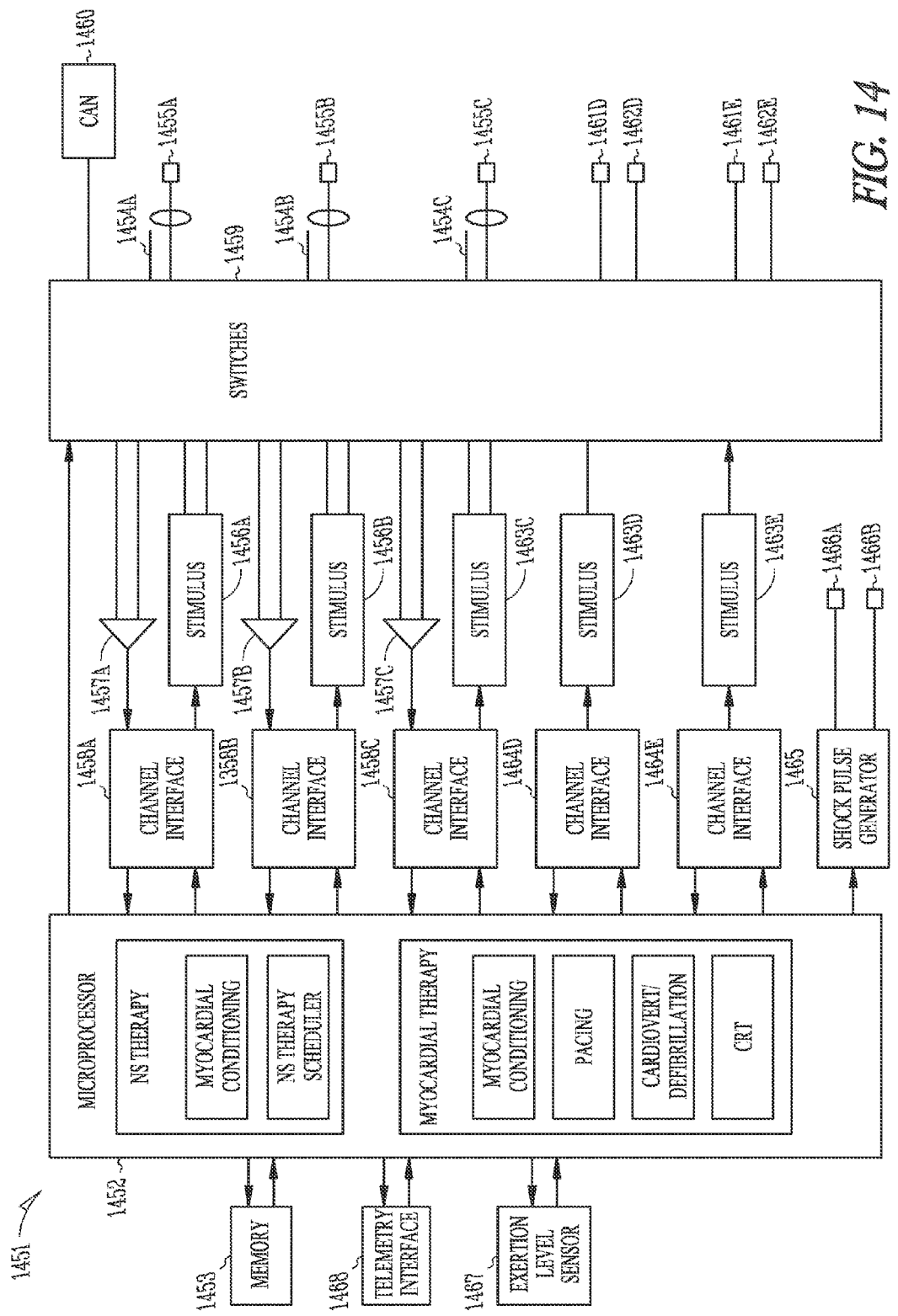
FIG. 14 shows a system diagram of an embodiment of a microprocessor-based implantable device.

FIG. 14 shows a system diagram of an embodiment of a microprocessor-based implantable device. The device 1451 is equipped with multiple sensing and pacing channels which may be physically configured to sense and/or pace multiple sites in the atria or the ventricles, and to provide neural stimulation. The illustrated device can be configured for myocardial stimulation (e.g. myocardium conditioning pacing, bradycardia pacing, defibrillation, CRT) and neural stimulation. The multiple sensing/pacing channels may be configured, for example, with one atrial and two ventricular sensing/pacing channels for delivering biventricular resynchronization therapy, with the atrial sensing/pacing channel used to deliver the biventricular resynchronization therapy in an atrial tracking mode as well as to pace the atria if required. The controller 1452 of the device is a microprocessor which communicates with memory 1453 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor.

Shown in FIG. 14, by way of example, are three sensing and pacing channels, such as can be used to provide myocardial stimulation/pacing, designated "A" through "C" comprising bipolar leads with ring, or proximal, electrodes 1454A-C and distal, or tip, electrodes 1455A-C, pulse generators 1456A-C, sensing amplifiers 1457A-C, and channel interfaces 1458A-C. Each channel thus includes a pacing channel made up of the pulse generator connected to the electrode and a sensing channel made up of the sense amplifier connected to the electrode. The channel interfaces 1458A-C communicate bidirectionally with the microprocessor 1452, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively. The pacing algorithms also include the appropriate preconditioning and postconditioning pacing algorithms.

The electrodes of each bipolar lead are connected via conductors within the lead to a switching network 1459 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring, or proximal, and tip, or distal, electrodes of a lead or in a unipolar mode using only one of the electrodes of the lead with the device housing or can 1460 serving as a ground electrode.

Also shown in FIG. 14, by way of example, are nerve stimulation channels designated "D" and "E." Neural stimulation channels are incorporated into the device. These channels can be used to deliver neural stimulation to elicit a parasympathetic and/or sympathetic response as part of a cardioprotective therapy, as discussed in this document. The illustrated channels include leads with electrodes 1461D and 1462D and electrodes 1461E and 1462E, a pulse generator 1463D and 1463E, and a channel interface 1464D and 1464E. The illustrated bipolar arrangement is intended as a non-exclusive example. Other neural stimulation electrode arrangements are within the scope of the present subject matter. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, pulse duration, and wave morphology, for example. A shock pulse generator 1465 is also interfaced to the controller for delivering a defibrillation shock via a pair of shock electrodes 1466A and 1466B to the atria or ventricles upon detection of a shockable tachyarrhythmia.

The illustrated controller includes a module for controlling neural stimulation (NS) therapy and module for controlling myocardial therapy. The NS therapy module can provide a variety of neural stimulation therapies, such as myocardial conditioning (e.g. vagal nerve stimulation or stimulation of a cardiac fat pad), antiarrhythmia and/or hypertension therapies, by way of example and not limitation. Also as illustrated, the myocardial therapy module includes a module for controlling myocardial conditioning pacing, a module for controlling bradycardia pacing therapies, a module for controlling defibrillation therapies, and a module for controlling CRT. The illustrated neural stimulation therapy module includes a myocardial conditioning module and a neural stimulation scheduling module. The scheduler controls the timing and duration of the stimulation. The controller controls the overall operation of the device in accordance with programmed instructions stored in memory, including controlling the delivery of paces via the pacing channels, interpreting sense signals received from the sensing channels, and implementing timers for defining escape intervals and sensory refractory periods. The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. CRT is most conveniently delivered in conjunction with a bradycardia pacing mode where, for example, multiple excitatory stimulation pulses are delivered to multiple sites during a cardiac cycle in order to both pace the heart in accordance with a bradycardia mode and provide pre-excitation of selected sites. An exertion level sensor 1467 (e.g., an accelerometer, a minute ventilation sensor, cardiac component of transthoracic and/or intracardiac impedance, or other sensor that measures a parameter related to metabolic demand) enables the controller to adapt the pacing rate in accordance with changes in the patient's physical activity and can enable the controller to modulate the delivery of neural stimulation and/or cardiac pacing. A telemetry interface 1468 is also provided which enables the controller to communicate with an external programmer or remote monitor.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by one or more processors cause the processor(s) to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system, comprising:
a myocardial stimulator adapted to deliver pacing pulses through at least one electrode to provide cardiac pacing;
at least one sensor adapted for use in detecting heart rate to determine heart rate turbulence (HRT);
a controller connected to the myocardial stimulator and the at least one sensor, wherein the controller is configured deliver a close-loop cardiac protective pacing therapy (CPPT) that intermittently stresses a heart to improve health through modulation of autonomic tone,
wherein in delivering the close-loop CPPT the controller is configured to:
intermittently deliver, using the myocardial stimulator, stress-inducing pacing pulses to the heart, wherein the intermittently delivered stress-inducing pacing pulses include sequences of stress-inducing pacing pulses to the heart to intentionally stress the heart to increase sympathetic tone during each of the sequences of stress-inducing pacing pulses, wherein the sequences are separated by time without stress-inducing pacing pulses;
monitor cardiac stress by determining, using the detected heart rate from the at least one sensor, HRT to assess the cardiac stress to the stress-inducing pacing pulses; and
adjust at least one parameter of the stress-inducing pacing pulses delivered for the CPPT to adjust the cardiac stress if the cardiac stress due to the stress-inducing pacing pulses is undesirable.

2. The system of claim 1, wherein the controller is configured to:
deliver a pacing pulse to elicit a premature ventricular contraction (PVC) during a time when the sequence of stress-inducing pacing pulses are not delivered; and
determine the heart rate turbulence response to the PVC.

3. The system of claim 2, wherein the controller is configured to determine HRT as a function of pre-PVC heart rate data and post-PVC heart rate data.

4. The system of claim 2, wherein the controller is configured to, after completion of the sequence of stress-inducing pacing pulses, deliver the pacing pulse to elicit the PVC and determine the HRT response to the PVC.

5. The system of claim 2, wherein the controller is configured to:
interrupt the sequence of stress-inducing pacing pulses before completion of the sequence of stress-inducing pacing pulses;
deliver the pacing pulse to elicit the PVC and determine the HRT response to the PVC after the sequence is interrupted; and
continue with the sequence of stress-inducing pacing pulses after the HRT response to the PVC is assessed.

6. The system of claim 1, wherein:
the sequence of stress-inducing pacing pulses are delivered as a treatment to adjust autonomic balance of a subject to a desired autonomic balance target; and
the controller is configured to monitor autonomic balance to assess efficacy of the treatment, and adjust at least one parameter of the stress-inducing pacing pulses based on the monitored autonomic balance to improve efficacy of the treatment.

7. The system of claim 6, wherein the controller is configured to adjust at least one parameter of the stress-inducing pacing pulses as a function of both the assessed cardiac stress to the stress-inducing pacing pulses and the assessed efficacy of the treatment.

8. The system of claim 1, wherein:
the at least one sensor adapted for use in determining HRT includes at least one sensor to sense a ventricular contraction; and
the controller is adapted to determine at least one RR interval immediately preceding a premature ventricular contraction and at least one RR interval immediately after of the PVC to determine HRT.

9. The system of claim 1, wherein the sequence of stress-inducing pacing pulses causes a paced heart to work harder in local regions away from a site where the stress-inducing pacing pulses are delivered than a non-paced heart.

10. The system of claim 1, wherein the sequence of stress-inducing pacing pulses pace at a rate faster than a rate of an intrinsic cardiac rhythm without the pacing pulses.

11. The system of claim 1, wherein the sequence of stress-inducing pacing pulses pace a ventricle with an AV delay that is shorter than an AV delay of an intrinsic cardiac rhythm without the pacing pulses.

12. The system of claim 1, wherein the sequence of stress-inducing pacing pulses pace a ventricle with a VV-delay that is longer than the VV delay of an intrinsic cardiac rhythm without the pacing pulses.

13. A system for delivering a close-loop cardiac protective pacing therapy (CPPT) that intermittently stresses a heart to improve health through modulation of autonomic tone, comprising:
means for intermittently delivering stress-inducing pacing pulses to the heart for the CPPT to intentionally stress the heart to increase sympathetic tone during the stress-inducing pacing pulses, wherein the intermittently delivered stress-inducing pacing pulses includes delivering sequences of stress-inducing pacing pulses where the sequences are separated by time without stress-inducing pacing pulses;

means for assessing cardiac stress to the stress-inducing pacing pulses delivered for the CPPT, wherein the means for assessing cardiac stress includes means for assessing heart rate turbulence (HRT), and the means for assessing HRT includes means for detecting heart rate using a sensor; and means for adjusting at least one parameter of the stress-inducing pacing pulses delivered for the CPPT to adjust cardiac stress if the cardiac stress to the stress-inducing pacing pulses is undesirable.

14. The system of claim 13, wherein the stress-inducing pacing pulses are delivered as a treatment to adjust autonomic balance of a subject to a desired autonomic balance target, the system further comprising means for assessing efficacy of the treatment, and means for adjusting at least one parameter of the stress-inducing pacing pulses based on the assessed efficacy to improve efficacy of the treatment.

15. The system of claim 13, wherein the means for assessing cardiac stress to the stress-inducing pacing pulses delivered for the CPPT includes:

means for delivering a pacing pulse to elicit a premature ventricular contraction (PVC) and assessing the heart rate turbulence response to the PVC after completion of one of the sequences of stress-inducing pacing pulses; or means for interrupting one of the sequences of stress-inducing pacing pulses before completion of the sequence of stress-inducing pacing pulses, delivering the pacing pulse to elicit the PVC and assessing the heart rate turbulence response to the PVC after the sequence is interrupted, and continuing with the sequence of stress-inducing pacing pulses after the heart rate turbulence response to the PVC is assessed.

16. A method, comprising: delivering a close-loop cardiac protective pacing therapy (CPPT) that intermittently stresses a heart to improve health through modulation of autonomic tone, wherein delivering the close-loop CPPT includes:

intermittently delivering stress-inducing pacing pulses to the heart for the CPPT to intentionally stress the heart to increase sympathetic tone during the stress-inducing pacing pulses, wherein intermittently delivering includes delivering sequences of stress-inducing pacing pulses where the sequences are separated by time without stress-inducing pacing pulses;

assessing cardiac stress to the stress-inducing pacing pulses delivered for the CPPT, wherein assessing cardiac stress includes determining heart rate turbulence, and determining heart rate turbulence includes detecting heart rate using a sensor; and if the assessed cardiac stress to the stress-inducing pacing pulses delivered for the CPPT is undesirable, adjusting at least one parameter of the stress-inducing pacing pulses to adjust cardiac stress.

17. The method of claim 16, wherein if the assessed cardiac stress to the stress-inducing pacing pulses is undesirably high, temporarily discontinuing the stress-inducing pacing pulses or adjusting at least one parameter of the stress-inducing pacing pulses to reduce cardiac stress to the stress-inducing pacing pulses.

18. The method of claim 17, wherein adjusting at least one parameter of the stress-inducing pacing pulses to reduce cardiac stress to the stress-inducing pacing pulses includes at least one of:

increasing an AV delay closer to an AV delay of an intrinsic cardiac rhythm without the pacing pulses;

shortening a VV delay closer to a VV delay of the intrinsic cardiac rhythm without the pacing pulses;

shortening a duration of the sequences of stress-inducing pacing pulses;

altering a pacing site; or decreasing the rate of the stress-inducing pacing pulses.

19. The method of claim 16, wherein if the assessed cardiac stress to the stress-inducing pacing pulses is undesirably low, adjusting at least one parameter of the stress-inducing pacing pulses to increase cardiac stress to the stress-inducing pacing pulses.

20. The method of claim 19, wherein adjusting at least one parameter of the stress-inducing pacing pulses to increase cardiac stress to the stress-inducing pacing pulses includes at least one of:

decreasing an AV delay further from an AV delay of an intrinsic cardiac rhythm without the pacing pulses;

lengthening a VV-delay further from a VV delay of the intrinsic cardiac rhythm without the pacing pulses;

lengthening a duration of the sequences of stress-inducing pacing pulses;

altering a pacing site;

increasing the rate of the stress-inducing pacing pulses; or discontinuing biventricular pacing in a patient with dyssynchrony to increase stress during the stress-inducing pacing pulses.

21. The method of claim 16, wherein:

delivering a sequence of stress-inducing pacing pulses includes at least one of:

pacing at a rate faster than a rate of an intrinsic cardiac rhythm without the pacing pulse; or pacing a ventricle with at least one of:

an AV delay, with or without a long VV delay, that is shorter than an AV delay of an intrinsic cardiac rhythm without the pacing pulses; or a VV delay that is longer than a VV delay of the intrinsic cardiac rhythm without the pacing pulses.

22. The method of claim 16, wherein adjusting parameters of the stress-inducing pacing pulses to adjust cardiac stress includes at least one of: adjusting a pacing rate, an AV delay, a VV delay, or a duration of the sequences of stress-inducing pacing pulses.

23. The method of claim 16, wherein assessing cardiac stress to the stress-inducing pacing pulses includes assessing a short-term autonomic balance response to the stress-inducing pacing pulses, the method further comprising assessing a long-term autonomic balance response to the stress-inducing pacing pulses.

24. The method of claim 23, wherein assessing the long-term autonomic balance response to the stress-inducing pacing pulses includes:

monitoring a value of at least one parameter and a progression of the at least one parameter to a desired goal; and determining a desired cardiac stress to the stress-inducing pacing pulses as a function of the monitored value and the desired goal for the at least one monitored parameter.

* * * * *